(12) United States Patent
Chang et al.

(10) Patent No.: US 6,384,104 B1
(45) Date of Patent: May 7, 2002

(54) METHOD FOR PREPARING ULTRAVIOLET RADIATION-ABSORBING COMPOSITIONS

(75) Inventors: Ching-Jen Chang, Ambler; Charles Elwood Jones, Yardley; Barry Weinstein, Dresher, all of PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 09/678,749

(22) Filed: Oct. 3, 2000

Related U.S. Application Data

(60) Provisional application No. 60/159,356, filed on Oct. 14, 1999.

(51) Int. Cl.$^7$ ............................ C08L 33/06; A61K 7/42; A61K 31/78
(52) U.S. Cl. ...................... 523/105; 523/135; 523/201; 524/458; 424/59; 424/60; 424/78.17
(58) Field of Search ................................. 523/105, 201, 523/135; 424/59, 60, 78.17; 524/458

(56) References Cited

U.S. PATENT DOCUMENTS

| | | | |
|---|---|---|---|
| 4,427,836 A | | 1/1984 | Kowalski et al. |
| 4,499,212 A | * | 2/1985 | Martino |
| 4,680,335 A | * | 7/1987 | Chambers et al. |
| 5,663,213 A | | 9/1997 | Jones et al. |

FOREIGN PATENT DOCUMENTS

| | | |
|---|---|---|
| EP | 669124 | 8/1995 |
| EP | 761201 | 3/1997 |

* cited by examiner

*Primary Examiner*—Tae H. Yoon
(74) *Attorney, Agent, or Firm*—Thomas J. Howell

(57) ABSTRACT

A method for improving the storage stability of personal care formulations containing ultraviolet (UV) radiation-absorbing agents (sunscreen agents) is disclosed. Latex polymer particles containing a void, having a particle size from 50 to 1000 nanometers, and having at least 4% polymerized crosslinker monomer units in the shell portion of the particle are especially effective in maintaining storage stability and effectiveness of sunscreen formulations when added to personal care compositions containing at least one sunscreen agent.

20 Claims, No Drawings

METHOD FOR PREPARING ULTRAVIOLET RADIATION-ABSORBING COMPOSITIONS

CROSS REFERENCE TO RELATED PATENT APPLICATIONS

This is a non-provisional application of prior pending U.S. provisional application Ser. No. 60/159,356 filed Oct. 14, 1999.

BACKGROUND

This invention relates to an improvement in the known process for enhancing the ultraviolet (UV) radiation absorption of personal care formulations, such as sunscreen compositions, where voided latex polymer particles are added to personal care compositions containing at least one UV radiation-absorbing agent. The improvement involves the use of selected polymer compositions for the latex polymer particles that results in extended stability as measured by retention of the SPF (Sun Protection Factor) enhancement and effectiveness under storage and use conditions.

Six percent of the solar energy reaching the earth's surface is ultraviolet (UV) radiation having a wavelength of 290–400 nanometers (nm). This radiation has two components: 5.5% UVA having a wavelength of 320–400 nm and 0.5% UVB having a wavelength of 290–320 nm. While the UV portion of the solar energy is relatively small, it induces nearly 99% of all the side effects of sunlight. UVB radiation, for example, is responsible for producing sunburn, aging and cancer of the skin. UVA radiation, for example, causes direct tanning and erythema (abnormal redness) and contributes to aging of the skin.

By avoiding exposure to sunlight, people can avoid the serious effects caused by UV radiation. However, because of the nature of their work, some people cannot avoid exposure to the sun. In addition, others voluntarily expose their skin to the sun to tan, sometimes to extremes. Therefore, protection against the harmful effects of the sun is important.

Protection from these harmful effects of UV radiation exposure is available in the form of topically applied formulations containing at least one physical blocker, or at least one chemical absorber, or combinations thereof. Physical blockers include active ingredients such as red petrolatum, titanium dioxide and zinc oxide. Chemical absorbers include active ingredients, such as para-aminobenzoic acid (more commonly known as PABA), which are generally transparent when applied and act by absorbing UV radiation, offering selective protection against certain UV wave bands.

The effectiveness of a sunscreen formulation is generally assessed by how well it protects the skin in terms of a Sun Protection Factor (SPF) which is defined as the ratio of the amount of energy required to produce a minimal erythema on sunscreen protected skin to the amount of energy required to produce the same level of erythema on unprotected skin.

A number of the chemical absorbers and physical blockers, hereafter referred to as "UV radiation-absorbing agents," typically used in sunscreen to formulations have adverse toxicological effects. Therefore, it is desirable to reduce the level of UV radiation-absorbing agents present in a sunscreen formulation without reducing the level of protection.

European Patent Applications EP 669,124 and EP 761,201 and U.S. Pat. No. 5,663,213 disclose the use of voided latex polymer particles having selected particle sizes to improve the absorbance of UV radiation in compositions containing one or more UV radiation-absorbing agents. U.S. Pat. No. 4,427,836 discloses processes for preparing core-shell polymers containing voids that are suitable for use as opacifying agents in coating compositions.

Although previous methods that reduce the level of UV radiation-absorbing agents in personal care formulations enhance initial SPF performance, there is a need for improved formulations that have extended lifetime and durability of the enhancement effect. The problem addressed by the present invention is to provide extended stability as measured by retention of the SPF (Sun Protection Factor) enhancement and effectiveness under storage and use conditions for the personal care formulations containing the particles and UV active ingredients.

STATEMENT OF INVENTION

The present invention provides a method for providing storage stability of UV radiation-absorption compositions, comprising adding to the compositions 5 to 70 percent of latex polymer particles, based on total weight nonvolatiles, to increase the UV radiation absorption of the compositions, wherein (a) the composition comprises at least one UV radiation-absorbing agent; (b) the latex polymer particles contain a void and have a particle size from 50 to 1000 nanometers; and (c) the latex polymer particles comprise a shell portion prepared by one or more steps selected from: (i) polymerization to incorporate from 4 to 80 percent monomeric units, based on total weight of the shell portion, of one or more polyethylenically unsaturated monomers; and (ii) polymerization to incorporate from 4 to 80 percent monomeric units, based on total weight of the shell portion, of one or more multifunctional monomers having at least one functional group capable of vinyl copolymerization and at least one functional group capable of reaction with a reactive molecule effective to produce post-polymerization crosslinking.

The present invention further provides a personal care composition comprising (a) at least one UV radiation-absorbing agent; and (b) from 5 to 70 percent of latex polymer particles, based on total weight nonvolatiles, comprising a shell portion prepared by polymerization to incorporate from 4 to 80 percent monomeric units, based on total weight of the shell portion, of one or more multifunctional monomers having at least one functional group capable of vinyl copolymerization and at least one functional group capable of reaction with a reactive molecule effective to produce post-polymerization crosslinking; wherein the composition has an SPF Enhancement Retention value of at least 40.

DETAILED DESCRIPTION

The compositions of the present invention are useful for improving the storage stability of personal care formulations containing at least one UV radiation-absorbing agent and latex polymer particles. We have found that selected crosslinker levels used in the shell portion of the latex polymer particles are particularly effective for this purpose and result in unexpectedly improved storage stability (as measured by the retention of SPF enhancement) and effectiveness of the personal care formulation as compared with the use of prior art latex polymer particles having little or no crosslinking in the shell portion of the polymer particles. These selected crosslinked shell compositions are based on (1) monomeric compositions containing polyethylenically unsaturated monomers, (2) monomeric compositions containing multifunctional monomers having at least one functional group capable of vinyl copolymerization and at least one functional group capable of reaction with suitable reactive molecules to produce post-polymerization crosslinking, or (3) combinations thereof.

As used herein, the term "(meth)acrylic" refers to either the corresponding acrylic or methacrylic acid and derivatives; similarly, the term "alkyl (meth)acrylate" refers to either the corresponding acrylate or methacrylate ester. As used herein, all percentages referred to will be expressed in weight percent (%), based on total weight of polymer or composition involved, unless specified otherwise. As used herein, the term "copolymer" or "copolymer material" refers to polymer compositions containing units of two or more different monomers. As used herein, the term "nonvolatiles" refers to solid or liquid components of the personal care formulation that do not readily evaporate at ambient temperatures due to their vapor pressure (such as polymer particles, UV radiation-absorbing agents and conventional adjuvants).

For the purposes of the present invention, the terms, "sheath" and "shell" are considered synonymous and refer to the total shell polymer composition (not including the core portion) prepared from single or multistage polymerizations.

For the purposes of the present invention, "SPF Enhancement Retention" (SER) refers to the retention (as a function of storage time) of the %SPF enhancement (%SE) of a sample containing latex particles relative to a control formulation containing no latex particles, expressed as a % value.

The method of the present invention includes incorporating from 5 to 70%, preferably from 10 to 50% and more preferably from 20 to 40%, based on total weight nonvolatiles in the personal care composition, of latex polymer particles into the composition containing at least one ultraviolet (UV) radiation-absorbing agent; based on total weight of the personal care composition, the level of latex polymer particles is from 0.5 to 10%, preferably from 1 to 7% and more preferably from 2 to 5%. As used herein, the term "UV radiation" includes both UVA and UVB radiation.

The latex polymer particles useful in the method of this invention have a particle size from 50 to 1000 nanometers (nm) (or 0.05 to 1 micron, $\mu$), typically from 100 to 600 nm (0.1 to 0.6 $\mu$), preferably from 200 to 500 nm (0.2 to 0.5 $\mu$), and more preferably from 300 to 400 nm (0.3 to 0.4 $\mu$), as measured by a Brookhaven BI-90 photon correlation spectrometer.

For a given particle size, it is desirable to produce latex polymer particles with a maximum void fraction as current processing techniques and particle integrity will permit. Typically, the latex polymer particles contain a void or voids with a void fraction from 1 to 70%, preferably from 5 to 50%, more preferably from 10 to 40%, and most preferably from 20 to 35%. The void fractions are determined by comparing the volume occupied by the latex polymer particles after they have been compacted from a dilute dispersion in a centrifuge to the volume of non-voided particles of the same composition.

The latex polymer particles useful in the invention can be prepared by conventional polymerization techniques such as sequential emulsion polymerization, including those processes disclosed in U.S. Pat. Nos. 4,427,836; 4,469,825; 4,594,363; 4,677,003; 4,920,160; and 4,970,241. The latex polymer particles may also be prepared, for example, by polymerization techniques disclosed in European Patent Applications EP 267,726, EP 331,421 and EP 915,108, or U.S. Pat. Nos. 4,910,229 and 5,157,084.

The latex polymer particles useful in the method of this invention can be formed from a multistaged particle comprising at least one core polymer and at least one shell polymer. The core polymer and shell polymers may each be made in a single polymerization step or in a sequence of polymerization steps. While the core may be made in single stage (or step) of the sequential polymerization and the shell may be the product of a single sequential step following the core stage, preparation of the core component may involve a plurality of steps in sequence followed by preparation of the shell, which may also involve a series of sequential steps. The amount of polymer deposited to form the shell portion or shell polymer is generally such as to provide an overall size of the finished multistage polymer particle of 0.05 to 1 micron. The ratio of the core weight to the total polymer particle weight is typically from 1/4 (25% core) to 1/100 (1% 30 core) and preferably from 1/8 (12% core) to 1/50 (2% core).

The monomers used in the emulsion polymerization of the "core" (or "seed") polymer of the latex polymer particles preferably include at least 5% of one or more monoethylenically unsaturated monomers containing at least one carboxylic acid group, based on total monomer weight of the core. The core polymer may be obtained, for example, by the emulsion homopolymerization of the monoethylenically unsaturated monomer containing at least one carboxylic acid group or by copolymerization of two or more of the monoethylenically unsaturated monomers containing at least one carboxylic acid group. Preferably, the monoethylenically unsaturated monomer containing at least one carboxylic acid group is copolymerized with one or more non-ionic (that is, having no ionizable group) ethylenically unsaturated monomers. The presence of the ionizable acid group makes the core swellable by the action of a swelling agent, such as an aqueous or gaseous medium containing a base to partially neutralize the acid core polymer and cause swelling by hydration.

The core polymer may optionally contain from 1 to 20% and preferably from 2 to 10%, based on the total monomer weight of the core, of polyethylenically unsaturated monomer, such as, for example, ethylene glycol di(meth) acrylate, allyl (meth)acrylate, 1,3-butanediol di(meth) acrylate, diethylene glycol di(meth)acrylate, trimethylolpropane tri(meth)acrylate and divinylbenzene. Alternatively, the core polymer may optionally contain from 0.1 to 60%, based on the total monomer weight of the core, of butadiene.

Suitable monoethylenically unsaturated monomers containing at least one carboxylic acid group useful in preparation of the "core" polymer, include, for example, acrylic acid, methacrylic acid, acryloxypropionic acid, (meth) acryloxypropionic acid, itaconic acid, aconitic acid, maleic acid or anhydride, fumaric acid, crotonic acid, monomethyl maleate, monomethyl fumarate and monomethyl itaconate. Acrylic acid and methacrylic acid are preferred carboxylic acid group-containing monomers.

Suitable non-ionic ethylenically unsaturated monomers useful in preparation of the "core" polymer, include, for example, styrene, vinyltoluene, ethylene, vinyl acetate, vinyl chloride, vinylidene chloride, acrylonitrile, (meth) acrylamide, ($C_1$–$C_{22}$)alkyl and ($C_3$–$C_{20}$)alkenyl esters of (meth)acrylic acid, such as methyl (meth)acrylate, ethyl (meth)acrylate, butyl (meth)acrylate, 2-ethylhexyl (meth) acrylate, benzyl (meth)acrylate, lauryl (meth)acrylate, oleyl (meth)acrylate, palmityl (meth)acrylate and stearyl (meth) acrylate.

The monomers used in the emulsion polymerization of the "shell" (or "sheath") polymer of the latex polymer particles preferably comprise one or more non-ionic ethylenically unsaturated monomers. Optionally, one or more monoethylenically unsaturated monomers containing at least one carboxylic acid group may be polymerized in the shell, such as, for example, acrylic acid, methacrylic acid, acryloxypropionic acid, methacryloxypropionic acid, aconitic acid, crotonic acid, maleic acid (and derivatives such as corresponding anhydride, amides and esters), fumaric acid (and derivatives such as corresponding amides and esters), itaconic and citraconic acids (and derivatives such as corresponding anhydrides, amides and esters); acrylic acid and methacrylic acid are preferred carboxylic acid group-containing monomers. When present in the shell polymer, the amount of carboxylic acid group-containing monomer units is from 0.1 to 10% is and more preferably from 0.5 to 5%, based on total weight of the shell portion of the polymer particle.

Optionally, one or more monoethylenically unsaturated monomers containing at least one "non-carboxylic" acid group may be polymerized in the shell, such as, for example, allylsulfonic acid, allylphosphonic acid, allyloxybenzenesulfonic acid, 2-acrylamido-2-methylpropanesulfonic acid (the acryonym "AMPS" for this monomer is a trademark of Lubrizol Corporation, Wickliffe, Ohio, USA), 2-hydroxy-3-(2-propenyloxy)propanesulfonic acid, 2-methyl-2-propene-1-sulfonic acid, 2-methacrylamido-2-methyl-1-propanesulfonic acid, 3-methacrylamido-2-hydroxy-1-propanesulfonic acid, 3-sulfopropyl acrylate, 3-sulfopropyl methacrylate, isopropenylphosphonic acid, vinylphosphonic acid, phosphoethyl methacrylate, styrenesulfonic acid, vinylsulfonic acid and the alkali metal and ammonium salts thereof. Preferred unsaturated "non-carboxylic" acid monomers are 2-acrylamido-2-methylpropanesulfonic acid and styrenesulfonic acid. When present in the shell polymer, the amount of unsaturated "non-carboxylic" acid monomer units is from 0.5 to 10% and more preferably from 1 to 5%, based on total weight of the shell portion of the polymer particle.

Suitable non-ionic ethylenically unsaturated monomers useful in preparing the shell polymer include, for example, vinyl acetate, acrylonitrile, methacrylonitrile, nitrogen-containing ring compound unsaturated monomers, vinylaromatic monomers, ethylenic monomers and selected (meth) acrylic acid derivatives. Preferably the shell portion of the latex polymer particles comprises as polymerized units from zero to 95% (meth)acrylic acid derivative monomer and from zero to 80% vinylaromatic monomer, based on total weight of the shell portion.

A preferred class of (meth)acrylic acid derivative is represented by $(C_1-C_{22})$alkyl (meth)acrylate, substituted (meth)acrylate and substituted (meth)acrylamide monomers. Each of the monomers can be a single monomer or a mixture having different numbers of carbon atoms in the alkyl portion. Preferably, the monomers are selected from one or more of $(C_1-C_4)$alkyl (meth)acrylates, hydroxy$(C_2-C_4)$ alkyl (meth)acrylates (such as hydroxyethyl methacrylate and hydroxypropyl methacrylate), dialkylamino$(C_2-C_4)$ alkyl (meth)acrylates (such as dimethylaminoethyl methacrylate) and dialkylamino$(C_2-C_4)$alkyl (meth) acrylamides (such as dimethylaminopropyl methacrylamide). The alkyl portion of each monomer can be linear or branched.

Examples of alkyl (meth)acrylate monomers where the alkyl group contains 1 to 4 carbon atoms include methyl methacrylate (MMA), methyl and ethyl acrylate, propyl methacrylate, butyl methacrylate (BMA), butyl acrylate (BA), isobutyl methacrylate (IBMA) and combinations thereof.

Examples of alkyl (meth)acrylate monomers where the alkyl group contains 10 or more carbon atoms include decyl methacrylate, isodecyl methacrylate, dodecyl methacrylate (also known as lauryl methacrylate), tetradecyl methacrylate (also known as myristyl methacrylate), pentadecyl methacrylate, hexadecyl methacrylate (also known as cetyl methacrylate), octadecyl methacrylate (also known as stearyl methacrylate), eicosyl methacrylate, behenyl methacrylate and combinations thereof.

Preferably the shell portion of the latex polymer particles comprises, as polymerized units, from 5 to 95%, more preferably from 10 to 80% and most preferably from 20 to 70%, based on total weight of the shell portion, of (meth) acrylic acid derivative monomer selected from one or more of methyl acrylate, methyl methacrylate, ethyl acrylate, ethyl methacrylate, butyl acrylate, butyl methacrylate, isobutyl acrylate, isobutyl methacrylate, hydroxyethyl methacrylate, hydroxypropyl methacrylate, dimethylaminoethyl methacrylate and dimethylaminopropyl methacrylamide.

Suitable vinylaromatic monomers include, for example, styrene, α-methylstyrene, vinyltoluene, alkyl-substititued styrene (such as t-butylstyrene and ethylvinylbenzene), halogenated styrenes (such as chlorostyrene and 3,5-bis (trifluoromethyl)styrene); styrene, ethylvinylbenzene and t-butylstyrene are preferred vinylaromatic monomers. When present in the shell polymer, the amount of vinylaromatic monomer units is from 1 to 80%, preferably from 5 to 70% and more preferably from 10 to 50%, based on total weight of the shell portion of the polymer particle.

Examples of nitrogen-containing unsaturated ring compound monomers include vinylpyridine, 2-methyl-5-vinylpyridine, 2-ethyl-5-vinylpyridine, 3-methyl-5-vinylpyridine, 2,3-dimethyl-5-vinylpyridine, 2-methyl-3-ethyl-5-vinylpyridine, methyl-substituted quinolines and isoquinolines, 1-vinylimidazole, 2-methyl-1-vinylimidazole, N-vinylcaprolactam, N-vinylbutyrolactam and N-vinylpyrrolidone.

Additional suitable monomers include ethylenic monomers (for example, ethylene, propylene, isobutylene, long chain alkyl α-olefins (such as $(C_{10}-C_{20})$alkyl α-olefins), vinyl halides (such as vinyl chloride, vinyl fluoride, vinyl bromide), vinylidene halides (such as vinylidene chloride and vinylidene fluoride), partially halogenated (meth) acrylates (such as 2-(perfluorododecyl)ethyl acrylate, 2-(perfluorododecyl)ethyl methacrylate, 2-(perfluorohexyl) ethyl acrylate, 2-(perfluorohexyl)ethyl methacrylate, hexafluoroisopropyl methacrylate, 2,2,3,3-tetrafluoropropyl acrylate and 2,2,2-trifluoroethyl methacrylate), and partially halogenated alkenes (such as 1,1,1-trifluoro-2,2-(trifluoromethyl)-butene).

The monomers that comprise the shell are selected to provide a glass transition temperature ($T_g$) in at least one shell which is high enough to support the void within the latex particle. Preferably the $T_g$ of at least one shell is greater than 50° C., more preferably greater than 60° C. and most preferably greater than 70° C., as measured by differential scanning calorimetry (DSC).

When the shell portion of the latex polymer particle is provided by a single stage polymerization process upon the core polymer, the entire shell portion produced may be referred to as the sheath, shell or "outermost" shell. However, when the shell portion is provided by a multistage polymerization process, then the "outermost" shell is defined by the composition of the final distinct polymerization stage used to prepare the latex particles. Typically, the "outermost" shell, when provided by a multistage polymerization process, will comprise at least about 25%, preferably at least 50% and more preferably at least 75% of the total shell portion of the latex polymer particle. Preferably, the crosslinking levels used to achieve the beneficial effects of the present invention are incorporated predominantly into the "outermost" shell of the latex particles. Crosslinker levels, unless indicated otherwise, are based on the total shell portion of the latex polymer particle, regardless of the number of stages used to prepare the latex particles.

The void of the latex polymer particles is preferably produced by swelling the acid core with an aqueous basic swellant that permeates the shell and expands the core. This expansion may involve partial merging of the outer periphery of the core into the pores of the inner periphery of the shell and also partial enlargement or bulging of the shell and the entire particle overall. When the swellant is removed by drying, the shrinkage of the core develops a microvoid, the extent of which depends on the resistance of the shell to restoration to its previous size. Suitable swelling agents for the core include, for example, ammonia, ammonium hydroxide, alkali metal hydroxides (such as sodium hydroxide), and volatile lower aliphatic amines (such as trimethylamine and triethylamine). The swelling step may occur during any of the multistage shell polymerization steps, between any of the staged polymerization steps, or at the end of the multistage polymerization process.

Crosslinking of the shell protion of the latex particles is required to achieve the enhanced storage stability of the UV radiation-absorption compositions. The crosslinking level is from 4 to 80%, preferably from 5 to 70%, more preferably from 10 to 60% and most preferably from 20 to 50%, based on total weight of the shell polymer portion of the latex particles. For latex particles based on multi-stage polymerization, it is preferable that the crosslinking take place predominantly in the "outermost" shell of the latex particle; typically, the crosslinking level is from 10 to 100%, preferably from 15 to 70% and more preferably from 20 to 60%, based on weight of the "outermost" shell polymer portion of the latex particles, where the crosslinking is based on polymerized monomer units of one or more polyethylenically unsaturated monomers and multifunctional monomers. At total shell crosslinking levels below about 4%, the crosslinking level is not sufficient to provide satisfactory SPF Enhancement Retention of formulated personal care formulations containing the latex particles.

Crosslinking in the shell can be derived from the use of one or more of the polyethylenically unsaturated monomers. Suitable polyethylenically unsaturated crosslinkers include, for example, di(meth)acrylates, tri(meth)acrylates, tetra (meth)acrylates, polyallylic monomers, polyvinylic monomers and (meth)acrylic monomers having mixed ethylenic functionality.

Di(meth)acrylates useful in the present invention include, for example, bis(1-acryloxy-2-hydroxypropyl)phthalate, bis (1-methacryloxy-2-hydroxypropyl)phthalate, bis(2-acryloxyethyl)phosphate, bis(2-methacryloxyethyl) phosphate, bis(acryloxy-2-hydroxypropyloxy)diethylene glycol, bis(methacryloxy-2-hydroxy-propyloxy)diethylene glycol, bisphenol A diacrylate, bisphenol A dimethacrylate, bisphenol A di-(3-acryloxyethyl) ether, bisphenol A di-(3-methacryloxyethyl) ether, bisphenol A di-(3-acryloxy-2-hydroxypropyl) ether, bisphenol A di-(3-methacryloxy-2-hydroxypropyl) ether, 1,3-butanediol diacrylate, 1,3-butanediol dimethacrylate, 1,4-butanediol di-(3-acryloxy-2-hydroxypropyl) ether, 1,4-butanediol di-(3-methacryloxy-2-hydroxypropyl) ether, 1,4-butanediol diacrylate, 1,4-butanediol dimethacrylate, 1,3-butanediol bis (acryloxypropionate), 1,3-butanediol bis (methacryloxypropionate), 1,4-butanediol bis (acryloxypropionate), 1,4-butanediol bis (methacryloxypropionate), 2-butene-1,4-diol diacrylate, 2-butene-1,4-diol dimethacrylate, 1,4-cyclohexanediol diacrylate, 1,4-cyclo-hexanediol dimethacrylate, 1,10-decanediol diacrylate, 1,10-decanediol dimethacrylate, diethylene glycol diacrylate, diethylene glycol dimethacrylate, 2,2-dimethyl-1,3-propanediol diacrylate, 2,2-dimethyl-1,3-propanediol dimethacrylate, dipentaerythritol ether acrylate, dipentaerythritol ether methacrylate, diphenolic acid di-(3-acryloxy-2-hydroxypropyl) ether, diphenolic acid di-(3-methacryloxy-2-hydroxypropyl) ether, dipropylene glycol diacrylate, dipropylene glycol dimethacrylate, 7,7,9-trimethyl-3,13-dioxo-3,14-dioxa-5, 12-diazahexadecane-1,16-diol diacrylate], 7,7,9-trimethyl-3,13-dioxo-3,14-dioxa-5,12-diazahexadecane-1,16-diol dimethacrylate, 1,12-dodecanediol diacrylate, 1,12-dodecanediol dimethacrylate, 1,2-ethanediol diacrylate, 1,2-ethanediol dimethacrylate, 1,2-ethanediol bis (acryloxypropionate), 1,2-ethanediol bis (methacryloxypropionate), 1,6-hexanediol diacrylate, 1,6-hexanediol dimethacrylate, 1,9-nonanediol diacrylate, 1,9-nonanediol dimethacrylate, 1,5-pentanediol diacrylate, 1,5-pentanediol dimethacrylate, 1,4-phenylenediacrylate, 1,4-phenylenedimethacrylate, 1-phenyl-1,2-ethanediol diacrylate, 1-phenyl-1,2-ethanediol dimethacrylate, polyoxyethyl-2,2-di(p-hydroxyphenyl)propane diacrylate, polyoxyethyl-2,2-di(p-hydroxyphenyl)propane dimethacrylate, 1,2-propanediol diacrylate, 1,2-propanediol dimethacrylate, 1,3-propanediol diacrylate, 1,3-propanediol dimethacrylate, propoxylated bisphenol A diacrylate, propoxylated bisphenol A dimethacrylate, tetrabromobisphenol A di-(3-acryloxy-2-hydroxypropyl) ether, tetrabromobisphenol A di-(3-methacryloxy-2-hydroxypropyl) ether, tetrachlorobisphenol A di-(3-acryloxy-2-hydroxypropyl) ether, tetrachlorobisphenol A di-(3-methacryloxy-2-hydroxypropyl) ether, tetraethylene glycol diacrylate, tetraethylene glycol dimethacrylate, triethylene glycol diacrylate, triethylene glycol dimethacrylate, 2,2,4-trimethyl-1,3-pentanediol diacrylate, 2,2,4-trimethyl-1,3-pentanediol dimethacrylate, tripropylene glycol diacrylate, and tripropylene glycol dimethacrylate. Additional suitable di(methacrylates) include, for example, aromatic fluorinated diacrylates (see U.S. Pat. No. 5,380,901 for further general and specific details), fluorinated diacrylates having structure 1,3-$[CH_2=CHCO_2CH_2CHOHCH_2OC(CF_3)_2]_2C_6H_3R_f$ where $R_f=C_1-C_{30}$ (see U.S. Pat. No. 4,914,171 for further general and specific details), fluorinated diacrylates (see European Patent Application EP 529,895 for further general and specific details), 1,3-bis(2-hydroxyhexafluoro-2-propyl) benzene diacrylate, 1,3-bis(2-hydroxyhexafluoro-2-propyl) benzene dimethacrylate, 1,3-bis(hydroxyperfluoroalkyl) benzene diacrylates and trifluoromethyl analogs of bisphenol A (meth)acrylates.

Tri(meth)acrylates useful in the present invention include, for example, 1,2,4-butanetriol triacrylate, 1,2,4-butanetriol trimethacrylate, glycerol triacrylate, lycerol trimethacrylate, pentaerythritol triacrylate, pentaerythritol trimethacrylate, polyoxypropyltrimethylolpropane triacrylate, polyoxypropyltrimethylolpropane trimethacrylate, silicone triacrylate, silicone trimethacrylate, 1,3,5-triacryloylhexahydro-s-triazine, 1,3,5-trimethacryloylhexahydro-s-triazine, trimethylolethane triacrylate, trimethylolethane trimethacrylate, 1,1,1-trimethylol propane triacrylate, 1,1,1-trimethylol propane trimethacrylate, 1,2,3-trimethylol propane triacrylate, 1,2,3-trimethylol propane trimethacrylate, 1,1,1-trimethylol propane tris(acryloxypropionate), 1,1,1-trimethylol propane tris(methacryloxypropionate), 1,2,3-trimethylol propane tris (acryloxypropionate), 1,2,3-trimethylol propane tris (methacryloxypropionate), tris-(2-acryloxyethyl) isocyanurate, tris-(2-methacryloxyethyl) isocyanurate.

Tetra(meth)acrylates useful in the present invention include, for example, pentaerythritol tetraacrylate, pentaerythritol tetramethacrylate, pentaerythritol tetrakis (acryloxypropionate), pentaerythritol tetrakis (methacryloxypropionate).

Polyallylic monomers useful in the present invention include, for example, diallyl carbonate, diallyl fumarate, diallyl glutarate, diallyl itaconate, diallyl maleate, diallyl phthalate, diallyl succinate, diisopropenylbenzene, triallyl cyanurate, triallyl isocyanurate, triallyl phosphate, and 1,3,5-triisopropenylbenzene.

Polyvinylic monomers useful in the present invention include, for example, diethyleneglycol divinyl ether, divinylbenzene, divinyl ketone, divinylpyridine, divinyl sulfide, divinyl sulfone, divinyltoluene, divinylxylene, glycerol trivinyl ether, trivinylbenzene, and 1,2,4-trivinylcyclohexane, N,N'-methylenebisacrylamide, partially fluorinated α,ω-dienes such as $CF_2=CFCF_2CF_2CH_2CH=CH_2$ (see PCT Patent Application WO 96/10047 for further general and specific details), trifluoroalkadienes (see U.S. Pat. No. 5,043,490 for further general and specific details), trifluorodivinylbenzenes (see U.S. Pat. No. 5,043,490 for further general and specific details) and fluorinated divinyl ethers of fluorinated 1,2-ethanediol (see U.S. Pat. No. 5,589,557 for further general and specific details). Preferably the polyvinylic monomer is divinylbenzene.

(Meth)acrylic monomers having mixed ethylenic functionalty that are useful as crosslinkers in the present invention include, for example, the acrylate ester of neopentyl glycol monodicyclopentenyl ether, allyl acryloxypropionate, allyl acrylate, allyl methacrylate, crotyl acrylate, crotyl methacrylate, 3-cyclohexenylmethyleneoxyethyl acrylate, 3-cyclohexenylmethyleneoxyethyl methacrylate, dicyclopentadienyloxyethyl acrylate, dicyclopentadienyloxyethyl methacrylate, dicyclopentenyl acrylate, dicyclopentenyl methacrylate, dicyclopentenyloxyethyl acrylate, dicycolpentenyloxyethyl methacrylate, methacrylate ester of neopentyl glycol monodicyclopentenyl ether, methallyl acrylate, trimethylolpropane diallyl ether mono-acrylate, trimethylolpropane diallyl ether mono-methacrylate and N-allyl acrylamide. Preferably the (meth)acrylic monomer having mixed ethylenic functionalty is allyl methacrylate.

Another route useful to crosslink the shell portion of the latex polymers is based on the use of one or more multifunctional monomers (MFM) to provide post-polymerization crosslinking and reinforcement of the sheath. The MFM comprise at least one functional group capable of vinyl copolymerization and at least one functional group capable of reaction with suitable reactive molecules. Suitable functional groups and reactive molecules for post-polymerization crosslinking of the polymer sheath include, for example, reacting polyol functional groups in the sheath with acid and aldehyde (such as formaldehyde) reactive molecules; reacting siloxane functional groups in the sheath with primary amine or amide reactive molecules; the addition of Zn (II) to polyacid functional groups in the sheath; irridation; heat curing of functional groups in sheath with or without additional initiator; and the addition of anhydride, isocyanate, epoxysiloxane, diepoxide (such as bisphenol A diglycidyl ether) and hydroxy acid reactive molecules to amine, alcohol and carboxylate functional groups which make up the sheath matrix.

MFM suitable for post-polymerization crosslinking include, for example, vinylsiloxanes, acryloylsiloxane, methacryloylsiloxanes, acetoacetoxyalkyl (meth)acrylates (such as acetoacetoxyethyl methacrylate or AAEM), N-alkylol (meth)acrylamides, epoxy (meth)acrylates (such as glycidyl methacrylate), acryloylisocyanates and methacryloylisocyanates. Suitable vinylsiloxanes include, for example, vinyltrimethoxysilane, vinyltriethoxysilane, vinytrioxypropylsilane, acrylamidopropyltrimethoxysilanes, methacrylamidopropyltrimethoxysilanes, styrylethyltrimethoxysilane and monomers known as Silquest™ silanes (Whitco Corp., Tarrytwon, N.Y., USA). Suitable acryloylsiloxanes and methacryloylsilanes include, for example, 3-acryloxypropyltrimethoxysilane, methacryloxypropyltrimethoxysilane, (3-acryloxypropyl) methyldialkoxysilanes and Silquest™ silanes. Suitable N-alkylol (meth)acrylamides include, for example, N-methylol acrylamide, N-methylol methacrylamide, N-butoxymethyl acrylamide, isobutoxymethyl acrylamide and methyl acrylamidoglycolate methyl ether. Preferably the MFM is selected from acetoacetoxyethyl methacrylate, N-methylol methacrylamide and glycidyl methacrylate.

A shell polymer based on MWF as described above may be reacted with reactive molecules selected from amines, diamines, amino acids and aminoalkyltrialkoxysilanes; optionally followed by the addition of other reactive molelcules: aldehydes (such as formaldehyde), dialdehydes (such as glutaric dialdehyde), hydrazides and dihydrazides (such as succinic dihydrazide) to form post-polymerization crosslinked sol-gels.

In addition to the latex polymer particles, the formulated compositions improved by the method of the present invention contain at least one UV radiation-absorbing agent. The UV radiation-absorbing agent may be incorporated into the formulated composition at a level to produce a desired sun protection factor. For example, the UV radiation-absorbing agent may be added to the formulated composition at a level of generally from 1 to 50%, preferably from 10 to 40% and more preferably from 20 to 35%, based on the total weight of nonvolatiles in the composition. Based on total weight of the formulated composition, the level of UV radiation-absorbing agent is generally from 0.5 to 25%, preferably from 2 to 20% and more preferably from 5 to 15%.

The UV radiation-absorbing agents used in the method of this invention are conventional materials. Suitable UV radiation-absorbing agents include, for example, oxybenzone, dioxybenzone, sulisobenzone, menthyl anthranilate, para-aminobenzoic acid, amyl paradimethylaminobenzoic acid, octyl para-dimethylaminobenzoate, ethyl 4-bis (hydroxypropyl) para-aminobenzoate, polyethylene glycol (PEG-25) para-aminobenzoate, ethyl 4-bis (hydroxypropyl) aminobenzoate, diethanolamine paramethyoxycinnamate, 2-ethoxyethyl paramethoxycinnamate, ethylhexyl para-methoxycinnamate, octyl para-methoxycinnamate, isoamyl paramethoxycinnamate, 2-ethylhexyl-2-cyano-3,3-diphenylacrylate, 2-ethylhexyl salicylate, homomenthyl salicylate, glyceryl aminobenzoate, triethanolamine salicylate, digalloyl trioleate, lawsone with dihydroxyacetone, 2-phenylbenzimidazole-5-sulfonic acid, 4-methylbenzylidine camphor, avobenzone, titanium dioxide and zinc oxide. Alternatively, UV absorbing agents such as triazines, benzotriazoles, vinyl group-containing amides, cinnamic acid amides and sulfonated benzimidazoles may also be used; European Patent Application EP 893,119 may be consulted for further general and specific details on these UV absorbing agents.

The compositions improved by the method of this invention may also include other conventional adjuvants used in UV absorbing compositions (although they may be optionally added to the formulated composition, water and volatile alcohol and hydrocarbon components are not included in this category). For example, if the composition is used as a sunscreen, it may additionally include film forming materials, emulsifiers, emollients, waterproofing agents, oils, stabilizers, thickeners, preservatives, perfume, colorants, insect repellants, self-tanning agents, humectants and combinations thereof. If the composition is used as a cosmetic, it may additionally include, for example, film forming materials, emulsifiers, softeners, self-tanning agents, humectants, emollients, oils, stabilizers, thickeners, preservatives, perfume, colorants, pigments and combinations thereof. Typically, the level of conventional adjuvants (when used) is generally from 1 to 70%, preferably from 5 to 50% and more preferably from 10 to 40%, based on the total weight of nonvolatiles in the composition; based on total weight of the formulated composition, the level of conventional adjuvants is generally from zero to 25%, preferably from 1 to 15% and more preferably from 3 to 12%.

The compositions improved by the method of this invention may be used in any application where protection from UV radiation is useful. For example, the improved composition may be used on human skin and hair, such as, for example personal care products, including, cosmetics, sunscreens, and hair care products. In addition, the method of this invention is also useful in improving the UV radiation-absorption storage stability of compositions for coatings on plant life, plastics, wood, for example in the form of a clear varnish.

The method of this invention may be used to improve the UV radiation-absorption storage stability of either clear or pigmented formulations. The method is particularly useful if a clear formulation is desired, such as a sunscreen formulation, because the addition of the latex polymer particles having a particle size of less than 500 nm, preferably less than 450 nm and more preferably less than 350 nm, does not significantly contribute to whiteness. The method of this invention enables formulators to either increase the UV radiation-absorbance of a given formulation or reduce the level of the UV radiation-absorbing agent present in the formulation while maintaining a given UV radiation-absorbance for extended periods of time.

While not wishing to be bound by theory, we believe that, in the case of the present invention, the crosslinked nature of the shell of the latex polymer particles improves the storage stability of the UV radiation-absorbing compositions by inhibiting the penetration of the shell, the uptake by the shell, or both, of oil-soluble additives present in the formulated composition (improved chemical resistance). When latex polymer particles are included in sunscreen formulations, where the shell portion of the particles is uncrosslinked or lightly crosslinked, the initial SPF enhancement effect (%SE) is apparent; however, the durability of the enhancement effect diminishes rapidly with time because of interaction of conventional adjuvants (for example, oils, emollients or the UV radiation-absorbing agent present in personal care formulations) with the latex polymer particle, destroying the integrity of the particles. However, when the shell is crosslinked to a level of at least 4% and preferably at least 10%, based on total weight of the shell polymer (as in the present invention), we believe that the detrimental effect of personal care composition additives on the duration of UV radiation-absorption enhancement is significantly reduced.

The compositions improved by the method of this invention may be applied to the skin at coating volumes, for example, of from about 0.5 microliters per square centimeter ($\mu l/cm^2$) to about 4 $\mu l/cm^2$.

Some embodiments of the invention are described in detail in the following Examples. All ratios, parts and percentages are expressed by weight unless otherwise specified, and all reagents used are of good commercial quality unless otherwise specified. The following abbreviations are used in the Examples:

MMA = Methyl Methacrylate
BMA = Butyl Methacrylate
ALMA = Allyl Methacrylate
MAA = Methacrylic Acid
/DVB = Divinylbenzene (80% active, 20% ethylvinylbenzene)
Sty = Styrene
SSS = Sodium Styrene Sulfonate
AAEM = Acetoacetoxyethyl Methacrylate
SDBS = Sodium Dodecylbenzenesulfonate
TMPTA = Trimethylolpropane Triacrylate
TEGDA = Tetraethyleneglycol Diacrylate
PBW = Parts by Weight
XL = Crosslinker
NA = Not Analyzed
MFM = Multifunctional Monomer The latex polymer particles and core polymer dispersions described in Examples 1 and 2 (and corresponding to Polymers #1–37) were prepared similarly to the method described in U.S. Pat. No. 4,427,836; core polymers typically had an average particle diameter of 90 to 150 nm (or 0.09 to 0.15 $\mu$) Polymer #1 is a control (comparative) polymer and is representative of polymer particles disclosed in U.S. Pat. No. 5,663,213. All polymer particle compositions listed below are based on 1 pbw core polymer corresponding to poly(MMA/MAA//60/40). Polymers #1–24 and #33–37 were prepared by the general method described in Example 1; polymers #25–32 were prepared by the general method described in Example 2.

Polymer #1
 Shell I: 5 pbw (88.5 MMA/8.5 BMA/3 MAA)
 Shell II: 18 pbw (99.75 Sty/0.25 ALMA)
Polymer #2
 Shell I: 5 pbw (88.5MMA/8.5 BMA/3 MAA)
 Shell II: 18.2 pbw (87.8 Sty/12.2 DVB)
Polymer #3
 Shell I: 5 pbw (88.5MMA/8.5 BMA/3 MAA)
 Shell II: 18.2 pbw (85.4 Sty/14.6 DVB)
Polymer #4
 Shell I: 5 pbw (88.5MMA/8.5 BMA/3 MAA)
 Shell II: 22.6 pbw (78.5 Sty/21.5 DVB)
Polymer #5
 Shell I: 5 pbw (88.5MMA/8.5 BMA/3 MAA)
 Shell II: 29.7 pbw (59.8 Sty/40.2 DVB)
Polymer #6
 Shell I: 5 pbw (88.5MMA/8.5 BMA/3 MAA)
 Shell II: 5.9 pbw (94.4 Sty/5.6 DVB)
 Shell III: 10.6 pbw (60.7 Sty/39.3 DVB)
Polymers #7, #33, #36 and #37

Shell I: 5 pbw (88.5MMA/8.5 BMA/3 MAA)
Shell II: 5.9 pbw (94.4 Sty/5.6 DVB)
Shell III: 10.6 pbw (48.8 Sty/51.2 DVB)
Polymer #8
　Shell I: 5 pbw (88.5MMA/8.5 BMA/3.0 MAA)
　Shell II: 5.9 pbw (94.4 Sty/5.6 DVB)
　Shell III: 10.6 pbw (29.5 Sty/2.8 SSS/67.7 DVB)
Polymer #9
　Shell I: 5 pbw (87.5 MMA/8.5 BMA/3 MAA/1 ALMA)
　Shell II: 18 pbw (99 MMA/1 ALMA)
Polymer #10
　Shell I: 3 pbw (87.5 MMA/8.5 BMA/3 MAA/1 ALMA)
　Shell II: 10 pbw (99 MMA/1 ALMA)
Polymer #11
　Shell I: 5 pbw (87.5 MMA/8.5 BMA/3 MAA/1 ALMA)
　Shell II: 18 pbw (97 MMA/3 ALMA)
Polymer #12
　Shell I: 5 pbw (87.5 MMA/8.5 BMA/3 ALMA)
　Shell II: 9 pbw (99 MMA/1 ALMA)
　Shell III: 9 pbw (99 MMA/4 ALMA)
Polymer #13
　Shell I: 5 pbw (87.5 MMA/8.5 BMA/3 MAA/1 ALMA)
　Shell II: 18 pbw (95 MMA/5 ALMA)
Polymer #14
　Shell I: 5 pbw (87.5 MMA/8.5 BMA/3 MAA/1 ALMA)
　Shell II: 9 pbw (99 MMA/1 ALMA)
　Shell III: 9 pbw (90 MMA/10 ALMA)
Polymer #15
　Shell I: 3 pbw (87.5 MMA/8.5 BMA/3 MAA/1 ALMA)
　Shell II: 11 pbw (90 MMA/10 ALMA)
Polymers #16 and #17
　Shell I: 3 pbw (83.5 MMA/8.5 BMA/3 MAA/5 ALMA)
　Shell II: 11 pbw (90 MMA/10 ALMA)
Polymer #18
　Shell I: 3 pbw (87.5 MMA/8.5 BMA/3 MAA/1 ALMA)
　Shell II: 11 pbw (80 MMA/20 ALMA)
Polymer #19
　Shell I: 5 pbw (87.5 MMA/8.5 BMA/3 MAA/1 ALMA)
　Shell II: 18 pbw (99 MMA/1 TEGDA)
Polymer #20
　Shell I: 5 pbw (87.5 MMA/8.5 BMA/3 MAA/1 ALMA)
　Shell II: 9 pbw (99 MMA/1 ALMA)
　Shell III: 9 pbw (96 MMA/1 ALMA/3 TEGDA)
Polymer #21
　Shell I: 5 pbw (87.5 MMA/8.5 BMA/3 MAA/1 ALMA)
　Shell II: 9 pbw (99 MMA/1 ALMA)
　Shell III: 9 pbw (96 MMA /4 TEGDA)
Polymer #22
　Shell I: 5 pbw (87.5 MMA/8.5 BMA/3 MAA/1 ALMA)
　Shell II: 9 pbw (99 MMA/1 ALMA)
　Shell III: 9 pbw (96 MMA/4 TMPTA)
Polymer #23
　Shell I: 5 pbw (87.5 MMA/8.5 BMA/3 MAA/1 ALMA)
　Shell II: 9 pbw (99 MMA/1 ALMA)
　Shell III: 9 pbw (90 MMA /10 TEGDA)
Polymer #24
　Shell I: 5 pbw (87.5 MMA/8.5 BMA/3 MAA/1 ALMA)
　Shell II: 9 pbw (99 MMA/1 ALMA)
　Shell III: 9 pbw (90 MMA/10 TMPTA)
Polymer #25
　Shell I: 5 pbw (87.2 MMA/8.7 BMA/3.1 MAA/1 ALMA)
　Shell II: 17.8 pbw (94 MMA/1 ALMA/5 AAEM)
Polymer #26
　Shell I: 5 pbw (87.5 MMA8.5 BMA/3 MAA/1 ALMA)
　Shell II: 20.4 pbw (86 MMA/1 ALMA,/13 AAEM)
Polymer #27
　Shell I: 5 pbw (87.5 MMA/8.5 BMA/3 MAA/1 ALMA)
　Shell II: 17.8 pbw (84 MMA/1 ALMA/15 AAEM)
Polymer #28
　Shell I: 5 pbw (87.5 MMA/8.5 BMA/3 MAA/1 ALMA)
　Shell II: 17.9 pbw (74 MMA/1 ALMA/25 AAEM)
Polymer #29
　Shell I: 5 pbw (87.5 MMA/8.5 BMA/3 MAA/1 ALMA)
　Shell II: 17.9 pbw (64 MMA/1 ALMA/35 AAEM)
Polymer #30
　Shell I: 5 pbw (87.5 MMA/8.5 BMA/3 MAA/1 ALMA)
　Shell II: 17.8 pbw (59 MMA/1 ALMA/40 AAEM)
Polymer #31
　Shell I: 5 pbw (87.5 MMA/8.5 BMA/3 MAA/1 ALMA)
　Shell II: 17.8 pbw (49 MMA/1 ALMA/50 AAEM)
Polymer #32
　Shell I: 5 pbw (87.5 MMA/8.5 BMA/3 MAA/1 ALMA)
　Shell II: 17.8 pbw (39 MMA/1 ALMA/60 AAEM)
Polymer #34
　Shell I: 5 pbw (88.5MMA/8.5 BMA/3 MAA)
　Shell II: 5.9 pbw (94.4 Sty/5.6 DVB)
　Shell III: 10.6 pbw (46 Sty/2.8 SSS/51.2 DVB)
Polymer #35
　Shell I: 5 pbw (89 MMA/9 BMA/3 MAA)
　Shell II: 5.9 pbw (94.4 Sty/5.6 DVB)
　Shell III: 10.6 pbw (46.1 Sty/2.7 SSS/51.2 DVB)

EXAMPLE 1

(Crosslinking with Polyethylenically Unsaturated Monomer)

To a 3-liter, 4-neck round bottom flask equipped with overhead stirrer, thermocouple, heating mantle, adapter inlet, Claisen head fitted with a water condenser and nitrogen inlet, and an inlet adapter, was added 630.50 grams (g) deionized water which was heated to 86° C. under nitrogen. To the heated water was added 0.96 g sodium persulfate in 6.88 g of deionized water followed by the addition of an aqueous dispersion of 31% poly(MMA/MAA//60/40) acrylic seed (core) polymer, having an average particle diameter of approximately 110 to 150 nm. To this heated mixture at 82° C. a monomer emulsion containing 23.75 g deionized water, 1.62 g aqueous solution of 23%SDBS, 66.72 g MMA, 6.34 g BMA and 2.20 g MAA was metered in over 90 minutes followed by a deionized water rinse. Next, a solution of 0.51 g sodium persulfate in 18.51 g deionized water was added over 90 minutes and the reaction temperature was raised to 90° C. concurrent with the addition of a second monomer emulsion containing 37.12 g deionized water, 1.02 g aqueous solution of 23%SDBS, 83.30 g Sty, 4.99 g DVB (80%) and 0.48 g linseed oil fatty acid, over 30 minutes. At the completion of addition of the second monomer emulsion 7.06 g aqueous 28% ammonium hydroxide was added. To the reaction mixture at 90° C. was added, over 60 minutes, a third monomer emulsion containing 66.03 g deionized water, 3.43 g aqueous solution of 23%SDBS, 77.44 g Sty and 81.13 g DVB (80%), followed by a deionized water rinse. The reactor contents were held at 90° C. for 30 minutes, 0.24 g sodium persulfate in 8.14 g deionized water was added, the reaction mixture was held at temperature for an additional 30 minutes, then cooled to 85° C. Next, 2.45 g of 0.15% $FeSO_4.7H_2O$ aqueous solution containing 0.25 g of 1% versene solution was added followed by the concurrent addition over 60 minutes of 2.41 g of t-butylhydrogen peroxide (70%) in 14.51 g of deionized water and 1.22 g isoascorbic acid in 14.73 g deionized water, to the reactor maintained at 80° C. The latex was cooled and then filtered. This description corresponds to the preparation of Polymer #7.

EXAMPLE 2
(Post-Polymerization Crosslinking with MFM)

Using the equipment described in the previous example, 630.80 g deionized water was charged to the reactor and heated to 86° C. under nitrogen. To the heated water was added 0.96 g sodium persulfate in 6.86 g deionized water followed by the addition of an aqueous dispersion of 31% poly(MMA/MAA/60/40) acrylic seed (core) polymer, having an average particle diameter of approximately 110 to 150 nm. To this heated mixture at 82° C. a monomer emulsion containing 23.66 g deionized water, 1.98 g aqueous solution of 23%SDBS, 65.12 g MMA, 6.33 g BMA, 2.21 g MAA and 0.77 g ALMA, was metered in over 90 minutes followed by a deionized water rinse. Next, a solution of 0.52 g sodium persulfate in 20.07 g deionized water was added over 90 minutes and the reaction temperature was raised to 88° C. concurrent with the addition, over 90 minutes, of a second monomer emulsion containing 112.11 g deionized water, 11.32 g aqueous solution of 23%SDBS, 156.39 g MMA, 2.72 g ALMA, 105.93 g AAEM and 1.32 g linseed oil fatty acid, followed by a water rinse. At the midpoint of the second monomer emulsion addition 40.00 g aqueous 28% ammonium hydroxide was added over 5 minutes. After completion of the second monomer emulsion addition the reactor contents were held at 88° C. for 10 minutes and then cooled to 85° C. Next, 2.42 g of a 0.15% $FeSO_4.7H_2O$ aqueous solution containing 0.24 g of a 1% versene solution was added followed by the concurrent addition over 60 minutes of 2.41 g of t-butylhydrogen peroxide (70%) in 14.59 g deionized water and 1.22 g isoascorbic acid in 14.65 g deionized water to the reactor maintained at 80° C. Then an aqueous solution of 42.00 g of 37% formaldehyde in 103.82 g deionized water was added over 30 minutes. After this addition the reaction mixture was held at 75–80° C. for 30 minutes, cooled to room temperature and filtered. This description corresponds to the preparation of Polymer #30.

EXAMPLE 3
(Storage Stability Evaluation of Latex Particles)

Compositions containing latex polymer particles useful in the present invention were evaluated for effectiveness in absorbing UV radiation to simulate different levels of sunscreen on human skin. The formulated compositions were prepared by adding the latex particles at a level of 5% (solid polymer), based on total weight of the formulated composition, to a sunscreen emulsion formulation. The emulsion formulation contained the following ingredients shown in Table 1 and was prepared as follows:

TABLE 1

| Phase | Ingredient | Parts by Weight (pbw) |
|---|---|---|
| A | deionized water | remainder to 100 pbw total |
| A | acrylates copolymer | 3.33 |

TABLE 1-continued

| Phase | Ingredient | Parts by Weight (pbw) |
|---|---|---|
| A | glycerin | 1.00 |
| A | tetrasodium EDTA | 0.10 |
| B | octylmethoxycinnamate | 6.00 |
| B | benzophenone-3 | 2.00 |
| B | ($C_{12}$–$C_{15}$)alkyl lactate | 2.00 |
| B | PVP/eicosene copolymer | 1.50 |
| B | cyclomethicone | 2.00 |
| B | stearic acid | 1.50 |
| C | triethanolamine 99% | 0.85 |
| D | latex polymer particles | 5.00 (as solids) |

Phase A components were mixed together and heated to 75° C. In a separate vessel Phase B components were mixed together and heated to 75° C. With adequate agitation, Phase B was mixed into Phase A. After complete mixing, Phase C was added to the A/B mixture and the mixture was then cooled to 40° C. while maintaining agitation. When the mixture was 40° C. or lower, Phase D (latex particles) was added as a dispersion, having been prepared by emulsion polymerization.

A control composition, hereinafter referred to as "Control," was also prepared according to the composition as shown in Table I, except that no latex polymer particles were added. The acrylates copolymer (as Aculyn™ 33 thickener from Rohm & Haas Company, Philadelphia, Pa.) was added to the composition to provide thickening; glycerin was added as a humectant; tetrasodium EDTA (ethylenediamine tetraacetic acetate) was added for mineral ion control; octylmethoxycinnamate and benzophenone-3 (as Escalol™ 557 and Escalol™ 567, respectively, from International Specialty Products (ISP)) were added as UV radiation-absorbing agents; ($C_{12}$–$C_{15}$)alkyl lactate (as Ceraphyl™ 41 from ISP) was added as an emollient and excipient; PVP/eicosene copolymer (as Ganex™ V-220 from ISP) was added as a waterproofing agent and a film-former; cyclomethicone (as Dow Corning 345 Fluid from Dow Corning) was added as an emollient and excipient; stearic acid was added as the emulsifier; and triethanolamine was added as a neutralizing agent for both the stearic acid and the acrylates copolymer.

The ability of the test composition to absorb UV radiation was evaluated by measuring the sun protection factor (SPF) of the test composition. The SPF was measured using an SPF 290 Analyzer with an integrating sphere and SPF Operating Software supplied by The Optometrics Group (Ayer, Mass., USA). The SPF 290 Analyzer measures the UV absorbance of a sample over UV radiation wavelengths (290–400 nm for each sample) and calculates an SPF value based on this UV absorbance spectrum. The following procedure for measuring SPF was used.

The compositions prepared were coated at a level of 0.038 millimeters (mm) or 1.5 mils, on quartz plates using a calibrated bird. This provided a very uniform film that is approximately equivalent to the film thickness for measuring SPF values on human skin (2 microliters per square centimeter) according to the test protocol from the FDA (64 Federal Register, 21 CFR, parts 310, 352, 700, 740; pages 27666–27693 (May 21, 1999)).

The SPF values were measured initially, after 1 week of storage of the formulated samples at 45° C. (±1° C.), and after 2 weeks of storage of the formulated samples at 45° C.; some samples were also evaluated after 4 weeks and 3 months. The "Control" was also measured and stored in the same manner. SER values were calculated as follows:

$$[SPF_s \text{ at time*}]-[SPF_c \text{ initial}]=\Delta SPF_s \text{ at time*}$$

$[SPF_s \text{ initial}] - [SPF_c \text{ initial}] = \Delta SPF_s \text{ initial}$ $SER = 100 \times [\Delta SPF_s \text{ at time}^* / \Delta SPF_s \text{ initial}]$ Where $\Delta SPF$=% enhancement in SPF relative to control formulation containing no latex particles; $SPF_s$, $\Delta SPF_s$, $SPF_c$, $\Delta SPF_c$=values for "sample" and "control," respectively; *storage time (for example, 1 week, 2 weeks, 4 weeks).

The accelerated aging tests described herein are believed to approximate the expected shelf-life for commercial formulations (containing latex particles of the present invention) stored at ambient temperatures: for example, 2 weeks at 45° C. is an estimate of shelf-life after 3 months; 4 weeks at 45° C. is an estimate of shelf-life after 1 year; and 3 months at 45° C. is an estimate of shelf-life after 3 years.

For the purposes of the present invention, the improvement in SPF Enhancement Retention (SER) provided by the crosslinked shell polymer compositions is represented by an SER value of at least 40, preferably at least 50, more preferably at least 75 and most preferably at least 90, as measured after 2 weeks at 45° C. Preferably, the formulated compositions also have SER values as indicated above, as measured after 4 weeks at 45° C. Tables 2,3, 4 and 5 summarize the effects of crosslinker level in the shell portion of the latex polymer particles on SER values as a function of storage time. Additional data: in Table 2, Polymer #7 had an SER value of 114 after 3 months at 45° C.; in Table 5, Polymer #31 had an SER value of 100 after 3 months at 45° C.

TABLE 2

(DVB crosslinker)

| Polymer # | % XL* | SER @ 45° C. (2 weeks) | SER @ 45° C. (4 weeks) |
|---|---|---|---|
| 1 | 0.2 (0.25) | 0 | 0 |
| 2 | 7.7 (9.8) | 53 | 33 |
| 3 | 9.2 (12) | 67 | 4 |
| 4 | 14 (17) | 77 | 73 |
| 5 | 28 (32) | 98 | 104** |
| 6 | 15.5 (34) | 109** | 115** |
| 7 | 21.5 (43.5) | 114** | 110** |
| 8 | 28 (57) | 119** | NA |

*% crosslinker in total shell portion (% crosslinker in outermost shell only).
**SER values of >100% are believed to be due to contribution (in addition to the effect of the latex particles) from more uniform distribution of the UV absorbing agent in the aged sample versus that of the initial control.

TABLE 3

(ALMA crosslinker)

| Polymer # | % XL* | SER @ 45° C. (2 weeks) | SER @ 45° C. (4 weeks) |
|---|---|---|---|
| 1 | 0.2 (0.25) | 0 | 0 |
| 9 | 1 (1) | 0 | 0 |
| 10 | 1 (1) | 0 | 0 |
| 11 | 2.6 (3) | 0 | 0 |
| 12 | 2.2 (4) | 0 | 0 |
| 13 | 4.1 (5) | 14 | 0 |
| 14 | 4.5 (10) | 57 | 28 |
| 15 | 8.1 (10) | 100 | 30 |
| 16 | 8.9 (10) | 71 | 0 |

TABLE 3-continued (ALMA crosslinker)

| Polymer # | % XL* | SER @ 45° C. (2 weeks) | SER @ 45° C. (4 weeks) |
|---|---|---|---|
| 17 | 8.9 (10) | 91 | 72 |
| 18 | 16 (20) | 74 | 91 |

* and **(see Table 2 footnotes)

TABLE 4

(miscellaneous acrylate crosslinkers)

| Polymer # | % XL* | SER @ 45° C. (1 week) | SER @ 45° C. (2 weeks) |
|---|---|---|---|
| 1 | ALMA 0.2 (0.25) | 0 | 0 |
| 19 | TEGDA 1 (1) | 0 | 0 |
| 20 | TEGDA 2.2 (4) | 18 | 0 |
| 21 | TEGDA 2.2 (4) | 14 | 0 |
| 22 | TMPTA 2.2 (4) | 11 | 0 |
| 23 | TEGDA 4.5 (10) | 44 | 45 |
| 24 | TMPTA 4.5 (10) | 104** | 60 |

* and ** (see Table 2 footnotes); % XL values in total shell portion include 0.6–1% ALMA for Polymers #20–24 and 0.2% ALMA for Polymer #19

TABLE 5

(post-polymerization crosslinking, AAEM)

| Polymer # | % XL* | SER @ 45° C. (2 weeks) | SER @ 45° C. (4 weeks) |
|---|---|---|---|
| 1 | 0.2 (0.25) | 0 | 0 |
| 25 | 4.9 (6) | 0 | 0 |
| 26 | 11 (14) | 11 | 0 |
| 27 | 13 (16) | 77 | 37 |
| 28 | 21 (26) | 112** | 112** |
| 29 | 28 (36) | 131** | 133** |
| 30 | 32 (41) | 138** | 138** |
| 31 | 40 (51) | 100 | 100 |
| 32 | 48 (61) | 100 | 100 |

* and ** (see Table 2 footnotes); % XL values in total shell portion include 1% ALMA for Polymers #25–32

EXAMPLE 4

(Particle Size Effects on SPF Enhancement and Opacity)

Composition containing latex polymer particles useful in the present invention were evaluated for effectiveness in absorbing UV radiation. The formulated compositions were prepared by adding the latex polymer particles at levels of 2–5% (solid polymer), based on total weight of the formulated composition, to a sunscreen emulsion formulation. The emulsion formulation contained the following ingredients shown in Table 6 and was prepared similarly to the procedure described in Example 3.

TABLE 6

| Phase | Ingredient | Parts by Weight (pbw) |
|---|---|---|
| A | deionized water | remainder to 100 pbw total |
| A | acrylates copolymer | 3.33 |
| A | glycerin | 1.00 |
| A | tetrasodium EDTA | 0.10 |
| B | octylmethoxycinnamate | 3.00 |
| B | benzophenone-3 | 1.00 |
| B | $(C_{12}-C_{15})$alkyl lactate | 2.00 |
| B | PVP/eicosene copolymer | 1.50 |
| B | cyclomethicone | 2.00 |

TABLE 6-continued

| Phase | Ingredient | Parts by Weight (pbw) |
|---|---|---|
| B | stearic acid | 1.50 |
| C | triethanolamine 99% | 0.85 |
| D | latex polymer particles | 2.00 to 5.00 (as solids) |

The procedure described in Example 3 was used for measuring SPF and determining %SPF Enhancement (%SE).

$$\%SPF \text{ Enhancement } (\%SE) = \frac{SPF(\text{sample}) - SPF(\text{control})}{SPF(\text{control})} \times 100$$

TABLE 7

(% SE versus particle size/loading level of polymer particles)

| | | % SE | | |
|---|---|---|---|---|
| Polymer # | Particle Size (nm) | 14% Polymer* | 23% Polymer* | 30% Polymer* |
| 33 | 294 | 40 | 55 | 97 |
| 34 | 320 | 69 | 101 | 154 |
| 35 | 361 | 93 | 190 | 290 |
| 36 | 414 | 203 | 358 | NA |
| 37 | 478 | 319 | NA | NA |

*% polymer particles, based on weight of nonvolatiles in formulation (corresponds to 2, 3.5 and 5%, respectively, based on total weight of formulation).

The data (Table 7) indicate that for a given latex polymer loading level, the %SE increases as the particle size increases and for a given particle size, the %SE increases as the loading level of dry polymer increases.

The samples were also measured for opacity by means of total light back-scattering using a helium-neon laser. The samples were compared to a standard sunscreen, Neutrogena™ Sensitive Skin Sunblock (from Neutrogena Corp), SPF 17, containing titanium dioxide. The ingredient listing for this product is: active ingredients (titanium dioxide); inactive ingredients (purified water, octyl palmitate, stearyl dimethicone, dimethicone, octyldodecyl neopentanoate, cyclomethicone, isoeicosane, polyglyceryl-4 isostearate, cetyl dimethicone copolyol, hexyl laurate, cetyl ricinoleate, isododecane, hydrolyzed soy protein, shea butter unsaponifiables, aluminum hydroxide, iron hydroxide, stearic acid, sodium chloride, diazolidinyl urea, methylparaben, ethylparaben and propylparaben). The opacity for each of the polymer samples at various loading levels versus the standard, which was given an opacity of 1.0, is listed in Table 8.

TABLE 8

(relative opacity versus particle size/loading level of polymer particles)

| | | Relative Opacity | | |
|---|---|---|---|---|
| Polymer # | Particle Size (nm) | 14% Polymer* | 23% Polymer* | 30% Polymer* |
| 33 | 294 | 0.4 | 0.4 | 0.5 |
| 34 | 320 | 0.4 | 0.5 | 0.7 |
| 35 | 361 | 0.6 | 0.8 | 1.1 |
| 36 | 414 | 0.9 | 1.4 | NA |
| 37 | 478 | 1.4 | NA | NA |

*% polymer particles, based on weight of nonvolatiles in formulation (corresponds to 2, 3.5 and 5%, respectively, based on total weight of formulation).

An increase in particle size of the latex particles, or an increase in loading level, increases the opacity of the formulation relative to the standard. The maximum relative opacity typically acceptable for use in personal care formulation is less than 1.3; for clear or transparent formulations, the desired range for relative opacity is less than 0.6. If the relative opacity is kept below approximately 1.0 and the %SE is maximized, then the maximum size for the particle is about 400 nm (at a loading level of 23%), and the minimum size range for a particle to provide a %SE of at least 50 is about 300 nm. For "clear" formulations, that is, those having a relative opacity of less than 0.6, the maximum particle size is up to about 320 nm for loading levels of 14–30%.

We claim:

1. A method for providing storage stability of UV radiation-absorption compositions, comprising adding to the compositions 5 to 70 percent of latex polymer particles, based on total weight nonvolatiles, to increase the UV radiation absorption of the compositions, wherein:
   (a) the composition comprises at least one UV radiation absorbing agent;
   (b) the latex polymer particles contain a void and have a particle size from 50 to 1000 nanometers; and
   (c) the latex polymer particles comprise a shell portion prepared by one or more steps selected from the group consisting of:
      (i) polymerization to incorporate from 4 to 80 percent monomeric units, based on total weight of the shell portion, of one or more polyethylenically unsaturated monomers; and
      (ii) polymerization, and post-polymerization crosslinking, to incorporate from 4 to 80 percent monomeric units, based on total weight of the shell portion, of one or more multifunctional monomers having at least one functional group capable of vinyl copolymerization and at least one functional group capable of reaction with a reactive molecule effective to produce post-polymerization crosslinking.

2. The method of claim 1 wherein the polyethylenically unsaturated monomers of step (c)(i) are selected from the group consisting of di(meth)acrylates, tri(meth)acrylates, tetra(meth)acrylates, polyallylic monomers, polyvinylic monomers, (meth)acrylic monomers having mixed ethylenic functionality and mixtures thereof.

3. The method of claim 1 wherein the shell portion of the latex polymer particles further comprises, as polymerized units, from 5 to 95 percent, based on total weight of the shell portion, of (meth)acrylic acid derivative monomer selected from the group consisting of methyl acrylate, methyl methacrylate, ethyl acrylate, ethyl methacrylate, butyl acrylate, butyl methacrylate, isobutyl acrylate, isobutyl methacrylate, hydroxyethyl methacrylate, hydroxypropyl methacrylate, dimethylaminoethyl methacrylate, dimethylaminopropyl methacrylamide and mixtures thereof.

4. The method of claim 1 wherein the shell portion of the latex polymer particles further comprises as polymerized units from 1 to 80 percent, based on total weight of the shell portion of the polymer particle, of vinylaromatic monomer.

5. The method of claim 1 wherein the latex polymer particles comprise an outermost shell comprising from 10 to 100 percent, based on weight of the outermost shell, of polymerized monomer units selected from the group consisting of the polyethylenically unsaturated monomers of step (c)(i), the multifunctional monomers of step (c)(ii) and mixtures thereof.

6. The method of claim 1 wherein the particle size of the latex polymer particles is from 100 to 600 nanometers.

7. The method of claim 1 wherein the UV radiation-absorbing agent is a chemical selected from the group consisting of oxybenzone, dioxybenzone, sulisobenzone, menthyl anthranilate, para-aminobenzoic acid, amyl para-dimethylaminobenzoic acid, octyl para-dimethylaminobenzoate, ethyl 4-bis-(hydroxypropyl) para-aminobenzoate, polyethylene glycol (PEG-25) para-aminobenzoate, ethyl 4-bis(hydroxypropyl)aminobenzoate, diethanolamine para-methyoxycinnamate, 2-ethoxyethyl para-methoxycinnamate, ethylhexyl para-methoxycinnamate, octyl para-methoxycinnamate, isoamyl para-methoxycinnamate, 2-ethylhexyl-2-cyano-3,3-diphenylacrylate, 2-ethylhexyl salicylate, homomenthyl salicylate, glyceryl aminobenzoate, triethanolamine salicylate, digalloyl trioleate, lawsone with dihydroxyacetone, 2-phenyl-benzimidazole-5-sulfonic acid, 4-methylbenzylidine camphor, avobenzone, titanium dioxide, zinc oxide, triazines, benzotriazoles, vinyl group-containing amides, cinnamic acid amides, sulfonated benzimidazoles and mixtures thereof.

8. A personal care composition comprising:
  (a) at least one UV radiation-absorbing agent; and
  (b) from 5 to 70 percent of latex polymer particles, based on total weight nonvolatiles, comprising a shell portion prepared by polymerization, and post-polymerization crosslinking, to incorporate from 4 to 80 percent monomeric units, based on total weight of the shell portion, of one or more multifunctional monomers having at least one functional group capable of vinyl copolymerization and at least one functional group capable of reaction with a reactive molecule effective to produce post-polymerization cross-linking;
wherein the composition has an SPF Enhancement Retention value of at least 40.

9. The method of claim 1 wherein the latex polymer particles are added to the composition to provide from 0.5 to 10 percent of latex polymer particles, based on total weight of the UV radiation-absorption composition.

10. The method of claim 1 wherein the composition has an SPF Enhancement Retention value of at least 40 percent, wherein SPF Enhancement Retention is defined as the retention of %SPF enhancement of a sample containing latex particles relative to a control formulation containing no latex particles, as a function of storage time, expressed as a percent value.

11. The method of claim 1 wherein the latex polymer particles have a void fraction of 1 to 70 percent.

12. The method of claim 11 wherein the void fraction is from 20 to 35 percent.

13. The method of claim 2 wherein the polyvinylic monomer is divinylbenzene.

14. The method of claim 2 wherein the (meth)acrylic monomer having mixed ethylenic functionality is allyl methacrylate.

15. A method for providing storage stability of UV radiation-absorption compositions, comprising adding to the compositions 5 to 70 percent of latex polymer particles, based on total weight nonvolatiles, to increase the UV radiation absorption of the compositions, wherein:
  (a) the composition comprises at least one UV radiation absorbing agent;
  (b) the latex polymer particles contain a void and have a particle size from 50 to 1000 nanometers; and
  (c) the latex polymer particles comprise a shell portion prepared by polymerization, and post-polymerization crosslinking, to incorporate from 4 to 80 percent monomeric units, based on total weight of the shell portion, of one or more multifunctional monomers having at least one functional group capable of vinyl copolymerization and at least one functional group capable of reaction with a reactive molecule effective to produce post-polymerization crosslinking; wherein the multifunctional monomers are selected from the group consisting of vinylsiloxanes, acryloylsiloxane, methacryloylsiloxanes, acetoacetoxyalkyl (meth) acrylates, N-alkylol (meth)acrylamides, epoxy (meth) acrylates, acryloylisocyanates, methacryloylisocyanates and mixtures thereof.

16. The method of claim 15 wherein the reactive molecule effective to produce post-polymerization crosslinking is selected from the group consisting of acid, aldehyde, primary amine, amide, anhydride, isocyanate, epoxysilane, diepoxide, hydroxyacid reactive molecules and mixtures thereof.

17. The method of claim 15 wherein the multifunctional monomer is selected from the group consisting of acetoacetoxyethyl methacrylate, N-methylol methacrylamide, glycidyl methacrylate and mixtures thereof.

18. The method of claim 4 wherein the vinylaromatic monomer is selected from the group consisting of styrene, ethylvinylbenzene, t-butylstyrene and mixtures thereof.

19. The method of claim 1, wherein the latex polymer particles are prepared as multistaged particles comprising at least one core polymer and at least one shell polymer, and wherein core polymer weight to total polymer particle weight is in a ratio from 1/4 to 1/100.

20. The method of claim 19, wherein the core polymer weight to total polymer particle weight is in a ratio from 1/8 to 1/50.

* * * * *